United States Patent
Ikeno et al.

(10) Patent No.: US 9,889,083 B2
(45) Date of Patent: Feb. 13, 2018

(54) 2-PART HAIR COSMETIC

(71) Applicant: Henkel AG & Co. KGaA, Duesseldorf (DE)

(72) Inventors: Fumika Ikeno, Tokyo (JP); Masaki Kawai, Ibaraki (JP); Shoji Machida, Tokyo (JP); Kota Uchida, Chiba (JP); Akira Matsutani, Chiba (JP); Maki Miyamoto, Tokyo (JP)

(73) Assignee: Henkel AG & Co. KGaA (DE)

( * ) Notice: Subject to any disclaimer, the term of this patent is extended or adjusted under 35 U.S.C. 154(b) by 268 days.

(21) Appl. No.: 14/698,992

(22) Filed: Apr. 29, 2015

(65) Prior Publication Data

US 2015/0231056 A1   Aug. 20, 2015

Related U.S. Application Data

(63) Continuation of application No. PCT/JP2013/072407, filed on Aug. 22, 2013.

(30) Foreign Application Priority Data

Oct. 31, 2012  (JP) .................. 2012-240770

(51) Int. Cl.
*A61Q 5/00* (2006.01)
*A61Q 5/10* (2006.01)
*A61K 8/86* (2006.01)
*A61K 8/41* (2006.01)
*A61K 8/34* (2006.01)
*A61K 8/22* (2006.01)
*A61Q 5/08* (2006.01)

(52) U.S. Cl.
CPC ............... *A61K 8/86* (2013.01); *A61K 8/22* (2013.01); *A61K 8/342* (2013.01); *A61K 8/415* (2013.01); *A61Q 5/08* (2013.01); *A61Q 5/10* (2013.01); *A61K 2800/4324* (2013.01); *A61K 2800/75* (2013.01); *A61K 2800/88* (2013.01)

(58) Field of Classification Search
CPC ... A61K 8/37; A61K 8/45; A61K 8/33; A61K 8/361; A61K 8/22; A61K 8/31; A61K 8/342; A61Q 8/05
See application file for complete search history.

(56) References Cited

U.S. PATENT DOCUMENTS

| | | | |
|---|---|---|---|
| 2002/0189034 A1 | 12/2002 | Kitabata et al. | |
| 2010/0154135 A1* | 6/2010 | Matsunaga | A61K 8/361 8/406 |

FOREIGN PATENT DOCUMENTS

| | | |
|---|---|---|
| JP | 2003-12473 A | 1/2003 |
| JP | 2003-34620 A | 2/2003 |
| JP | 2003-201225 A | 7/2003 |
| JP | 2005-162665 A | 6/2005 |
| JP | 2010-254633 A | 11/2010 |
| JP | 2012-97024 A | 5/2012 |

OTHER PUBLICATIONS

PCT International Search Report (PCT/JP2013/072407) dated Oct. 25, 2013.
Nikko Chemicals Co. Ltd., Shin Keshohin Handbook, pp. 578-582, 2006 (English Translation).

* cited by examiner

*Primary Examiner* — Nannette Holloman
(74) *Attorney, Agent, or Firm* — P. Scott Smith

(57) ABSTRACT

The present invention provides a two-part hair cosmetic material having a reduced irritating smell due to ammonia. Specifically, the present invention relates to a two-part hair cosmetic material comprising a first agent containing an alkali agent and a second agent containing an oxidizing agent, wherein the first agent contains the following ingredients: (A) a polyoxyethylene alkyl ether having a polyoxyethylene chain length of 50 or more, (B) a higher alcohol, and (C) a polyoxyethylene alkyl ether having a polyoxyethylene chain length shorter than the polyoxyethylene chain length of the polyoxyethylene alkyl ether (A), and the content of a higher alcohol having 20 or more carbon atoms in the higher alcohol (B) is 1.0% by weight or less based on the weight of the first agent.

19 Claims, No Drawings

2-PART HAIR COSMETIC

FIELD OF THE INVENTION

The present invention generally relates to a two-part hair cosmetic material which is excellent in applicability to the hair and is reduced in the irritating smell due to ammonia.

BACKGROUND OF THE INVENTION

A two-part hair cosmetic material comprises a first agent containing an alkali agent such as ethanolamine, a carbonate and ammonia, and a second agent containing an oxidizing agent such as hydrogen peroxide. Both the agents are mixed together immediately before use to give a hair cosmetic material, and the hair cosmetic material is applied to the hair to bleach or dye the hair.

Among the above-mentioned alkali agents, ethanolamine may have defects such as hair damage and skin irritation since it is very persistent on the hair. Further, since a carbonate is weak in the effect of enhancing bleaching power or hair dyeing power due to hydrogen peroxide, bright coloration of the hair may become insufficient. To the contrary, since ammonia does not remain in the hair, and further can sufficiently enhance bleaching power or dyeing power due to hydrogen peroxide, it is most generally used in a two-part hair cosmetic material for bleaching or dyeing.

However, ammonia may emit a peculiar irritating smell that gives discomfort to a user when a first agent and a second agent are mixed together, or when a hair cosmetic material obtained by mixing both the agents together is applied to the hair. Particularly, when the blending amount of ammonia is increased in order to sufficiently bleach or dye the hair, a more overpowering irritating smell may be emitted to give discomfort to the user.

In order to solve these problems, a variety of methods have been reported. For example, a composition which reduces an irritating smell due to ammonia is known, which is obtained by incorporating an alkali agent into a liquid crystal structure of a hair cosmetic material (JP-A-2003-40750 and JP-A-2004-189638).

However, in the conventional composition utilizing a liquid crystal structure, there is a problem that the degree of freedom of formulation is restricted in order to attain a stable emulsion state and reduce an irritating smell due to ammonia. Particularly, there may arise a problem that, when the viscosity of the hair cosmetic material is reduced in order to provide a hair cosmetic material which can be easily spread on the whole hair uniformly and which has good combability (comb through property) when it is adapted to the hair again during the time after the application, an irritating smell due to ammonia cannot be reduced, for example. Further, there may arise a problem that an irritating smell due to ammonia becomes further stronger in a case where strong bleaching power or dyeing power is required and ammonia in an amount sufficient for the desired bleaching or dyeing effect is added to the hair cosmetic material.

The present invention solves the above-mentioned problems of the conventional techniques, and an object thereof is to provide a two-part hair cosmetic material which is reduced in the irritating smell due to ammonia, and is good in applicability of a hair cosmetic material obtained by mixing a first agent and a second agent together to the hair, and comb through property. Another object of the present invention is to provide a two-part hair cosmetic material of which emulsified state is stable, and which is reduced in the irritating smell due to ammonia even if it contains ammonia in such an amount that the hair can be sufficiently bleached or dyed with the hair cosmetic material.

Furthermore, other desirable features and characteristics of the present invention will become apparent from the subsequent detailed description of the invention and the appended claims, taken in conjunction with the accompanying drawings and this background of the invention.

Brief Summary of the Invention

A two-part hair cosmetic material comprising a first agent containing an alkali agent and a second agent containing an oxidizing agent, wherein the first agent contains the following ingredients: (A) a polyoxyethylene alkyl ether having a polyoxyethylene chain length of 50 or more; (B) a higher alcohol; and (C) a polyoxyethylene alkyl ether having a polyoxyethylene chain length shorter than the polyoxyethylene chain length of the polyoxyethylene alkyl ether (A), and the content of a higher alcohol having 20 or more carbon atoms in the higher alcohol (B) is 1.0% by weight or less based on the weight of the first agent.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The present inventors found out that the following two-part hair cosmetic material of the present invention attains the above-mentioned objects:

a two-part hair cosmetic material comprising a first agent containing an alkali agent and a second agent containing an oxidizing agent, wherein the first agent contains the following ingredients:

(A) a polyoxyethylene alkyl ether having a polyoxyethylene chain length of 50 or more, (B) a higher alcohol, and (C) a polyoxyethylene alkyl ether having a polyoxyethylene chain length shorter than the polyoxyethylene chain length of the polyoxyethylene alkyl ether (A), and the content of a higher alcohol having 20 or more carbon atoms in the higher alcohol (B) is 1.0% by weight or less based on the weight of the first agent.

Examples of specific embodiments of the hair cosmetic material of the present invention include the following:

(1) A two-part hair cosmetic material comprising a first agent containing an alkali agent and a second agent containing an oxidizing agent, wherein the first agent contains the following ingredients:

(A) a polyoxyethylene alkyl ether having a polyoxyethylene chain length of 50 or more, (B) a higher alcohol, and (C) a polyoxyethylene alkyl ether having a polyoxyethylene chain length shorter than the polyoxyethylene chain length of the polyoxyethylene alkyl ether (A), and the content of a higher alcohol having 20 or more carbon atoms in the higher alcohol (B) is 1.0% by weight or less based on the weight of the first agent.

(2) The two-part hair cosmetic material according to (1), wherein the higher alcohol (B) comprises at least two kinds of higher alcohols selected from higher alcohols having less than 20 carbon atoms.

(3) The two-part hair cosmetic material according to (1) or (2), wherein the higher alcohol (B) does not comprise a higher alcohol having 20 or more carbon atoms.

(4) The two-part hair cosmetic material according to any one of (1) to (3), wherein the two-part hair cosmetic material is a two-part hair cosmetic material for dyeing.

(5) The two-part hair cosmetic material according to any one of (1) to (4), wherein the ingredient (A) is a polyoxyethylene alkyl ether having a polyoxyethylene chain length of 80 or more.

(6) The two-part hair cosmetic material according to any one of (1) to (5), wherein the first agent further comprises a cationic surfactant.

According to the two-part hair cosmetic material of the present invention, a liquid crystal structure is formed, an alkali agent such as ammonia is retained in a hydrophilic portion, a lipophilic portion surrounds the hydrophilic portion, the alkali agent is enclosed, and an irritating smell due to ammonia can be reduced. However, the present invention is not limited to the above-mentioned mechanism.

Further, the two-part hair cosmetic material of the present invention has good applicability to the hair and comb through property, and a hair cosmetic material obtained by mixing the first agent and the second agent together can be easily spread on the whole hair uniformly.

In addition, the two-part hair cosmetic material of the present invention has high degree of freedom of formulation, and usually has sufficient emulsion stability even when a dye, an alkali agent, an oil agent or a salt which destabilizes emulsification is blended therein. Particularly, even when the cosmetic material contains an ingredient which usually destabilizes particularly emulsification, such as a dye being a salt, for example, paraphenylenediamine hydrochloride, toluene-2,5-diamine sulfate or the like, and an alkali agent being a salt, for example, ammonium carbonate, ammonium bicarbonate or the like, sufficient emulsion stability and operability can be ensured, and an irritating smell due to ammonia can be reduced. Further, even when the cosmetic material contains ammonia in an amount sufficient for bleaching or dyeing the hair, the emulsified state is stable, and an irritating smell can be reduced.

Further, according to the two-part hair cosmetic material of the present invention, since the cosmetic material has sufficient emulsion stability and can sufficiently reduce an irritating smell due to ammonia even at a relatively low viscosity, a hair cosmetic material which has excellent mixability, applicability and comb through property, as well as a reduced irritating smell due to ammonia and good emulsion stability can be provided.

Embodiments of the present invention will be described. The two-part hair cosmetic material of the present invention comprises a first agent containing an alkali agent and a second agent containing an oxidizing agent, as described above.

Alkali Agent

In the two-part hair cosmetic material of the present invention, the first agent contains an alkali agent in order to swell the hair, impregnate a dye into the hair, and improve hair bleaching power.

The first agent of the two-part hair cosmetic material of the present invention usually contains ammonia as the alkali agent. The first agent may contain ammonia alone, or may contain other alkali agents together with ammonia, without any limitation. Examples of the alkali agents which may be used together with ammonia include alkanolamines such as monoethanolamine (MEA), diethanolamine (DEA), triethanolamine (TEA), 2-amino-2-methyl-1-propanol (AMP), 2-amino-2-methyl-1,3-propanediol (AMPD), tetrakis(2-hydroxyisopropl)ethylenediamine (TE), and monoisopropanolamine (MIPA), ammonium carbonate, ammonium bicarbonate, sodium carbonate, potassium carbonate, sodium phosphate, disodium hydrogen phosphate, sodium hydroxide, and potassium hydroxide. Ammonium carbonate and ammonium bicarbonate are preferable since more excellent swelling of the hair, impregnation of a hair dye, and bleaching of the hair are achieved. One kind of these alkali agents may be used together with ammonia, or a combination of two or more kinds thereof may be used together with ammonia.

The content of the alkali agent is appropriately set according to the desired bleaching power or dyeing power, and is not particularly limited. However, when higher bleaching power or dyeing power is desired, in order to sufficiently swell the hair, impregnate the hair cosmetic material into the hair, and sufficiently bleach the hair, the content is preferably 0.1% by weight or more, more preferably 1% by weight or more, and particularly preferably 2% by weight or more, in terms of 28% aqueous ammonia, based on the total weight of the first agent and the second agent. On the other hand, in order to more alleviate irritation to the scalp and damage of the hair, the content is preferably 10% by weight or less, and more preferably 7% by weight or less, in terms of 28% aqueous ammonia, based on the total weight of the first agent and the second agent.

Oxidizing Agent

In the two-part hair cosmetic material of the present invention, the second agent contains an oxidizing agent which is usually used in the field of two-part hair cosmetic materials.

The oxidizing agent is not particularly limited, and examples thereof include hydrogen peroxide, sodium perborate, potassium perborate, sodium percarbonate, and sodium bromate. Among them, particularly, hydrogen peroxide is preferable since a hair cosmetic material having sufficient hair dyeing power and bleaching power is obtained. The second agent may contain these oxidizing agents alone, or may contain a combination of two or more kinds thereof The content of the oxidizing agent is appropriately set according to the desired bleaching power and dyeing power, the amount required for oxidizing all of an oxidation dye, and the like, and is not particularly limited. However, when higher bleaching power or dyeing power is desired, the content is preferably 0.01% by weight or more, and more preferably 0.1% by weight or more based on the total weight of the first agent and the second agent. On the other hand, even when the second agent contains the oxidizing agent in an amount exceeding 15% by weight based on the total weight of the first agent and the second agent, the dyeing power is not improved any more. Therefore, the content is preferably 15% by weight or less, and more preferably 10% by weight or less based on the total weight of the first agent and the second agent.

In the two-part hair cosmetic material of the present invention, the first agent further contains, in addition to the above-mentioned ingredients, (A) a polyoxyethylene alkyl ether having a polyoxyethylene chain length of 50 or more, (B) a higher alcohol, and (C) a polyoxyethylene alkyl ether having a polyoxyethylene chain length shorter than the polyoxyethylene chain length of the polyoxyethylene alkyl ether (A).

The ingredient (A) a polyoxyethylene alkyl ether having a polyoxyethylene chain length of 50 or more is not particularly limited, and examples thereof include polyoxyethylene (50) lauryl ether, polyoxyethylene (150) cetyl ether, polyoxyethylene (50) stearyl ether, polyoxyethylene (80) stearyl ether, polyoxyethylene (100) stearyl ether, polyoxyethylene (50) cetyl stearyl ether, polyoxyethylene (50) oleyl ether, polyoxyethylene (55) cetyl stearyl ether, polyoxyethylene (60) cetyl stearyl ether, polyoxyethylene (80) cetyl stearyl ether, polyoxyethylene (82) oleyl ether, and polyoxyethylene (106) oleyl ether.

The polyoxyethylene chain length of the ingredient (A) is preferably 55 or more, and more preferably 80 or more, in order to reduce an irritating smell due to ammonia and ensure good emulsion stability. On the other hand, the polyoxyethylene chain length is preferably 150 or less. A polyoxyethylene alkyl ether having a polyoxyethylene chain length of 100 is particularly preferable since it has an effect of sufficiently reducing an irritating smell due to ammonia, and emulsion stability can be ensured with high degree of freedom of formulation. Among them, polyoxyethylene (100) stearyl ether is extremely preferable since the effect of reducing an irritating smell due to ammonia is higher, the degree of freedom of formulation is high, and good emulsion stability can be ensured even when a sufficient amount of a dye is contained in order to dye the hair deeply, for example.

The first agent may contain these polyoxyethylene alkyl ethers having a polyoxyethylene chain length of 50 or more alone, or a combination of two or more kinds thereof.

The content of the ingredient (A) is appropriately set in such a range that the effect of the present invention is exerted, and is not particularly limited. However, the content is preferably 0.1% by weight or more, and more preferably 0.5% by weight or more based on the total weight of the first agent and the second agent since the effect of reducing an irritating smell due to ammonia is higher, and better emulsion stability and applicability can be ensured. On the other hand, the content of the ingredient (A) is preferably 10% by weight or less, and more preferably 8% by weight or less based on the total weight of the first agent and the second agent since the effect of reducing an irritating smell due to ammonia is higher, and better emulsion stability and applicability can be ensured.

The ingredient (B) is not particularly limited, and examples thereof include higher alcohols such as lauryl alcohol, myristyl alcohol, cetanol, stearyl alcohol, cetostearyl alcohol, behenyl alcohol, isostearyl alcohol, oleyl alcohol, hexyldecanol, and octyldodecanol. A higher alcohol having 12 or more carbon atoms is preferable since a better liquid crystal structure is formed, and an irritating smell due to ammonia is more reduced. On the other hand, a higher alcohol having less than 20 carbon atoms is preferable since a better liquid crystal structure is formed and an irritating smell due to ammonia is more reduced, and good applicability of the hair cosmetic material to the hair is obtained. A higher alcohol having 14 to 18 carbon atoms is more preferable.

The two-part hair cosmetic material of the present invention may contain the higher alcohols alone, or a combination of two or more kinds thereof as the ingredient (B). By inclusion of a combination of two or more kinds of higher alcohols preferably having less than 20 carbon atoms, more preferably having 14 to 18 carbon atoms, better applicability is obtained. Particularly, it is extremely preferable from the view point of reduction in an irritating smell due to ammonia, and applicability to the skin and comb through property of the hair cosmetic material that the two-part hair cosmetic material of the present invention contains two or more kinds of higher alcohols selected from the group consisting of myristyl alcohol, cetanol and stearyl alcohol as the ingredient (B).

The content of the ingredient (B) is not particularly limited. However, the content is preferably 1.0% by weight or more, and more preferably 2.0% by weight or more based on the total weight of the first agent and the second agent since the effect of reducing an irritating smell due to ammonia is higher, and better emulsion stability and good applicability to the hair can be ensured. On the other hand, the content of the ingredient (B) is preferably 20% by weight or less, and more preferably 15% by weight or less based on the total weight of the first agent and the second agent since the effect of reducing an irritating smell due to ammonia is higher, and better emulsion stability and applicability to the hair can be ensured.

When the two-part hair cosmetic material of the present invention contains a higher alcohol having 20 or more carbon atoms as the higher alcohol of the ingredient (B), the content of the higher alcohol having 20 or more carbon atoms is 1.0% by weight or less based on the weight of the first agent. When the content of the higher alcohol having 20 or more carbon atoms is more than 1.0% by weight based on the weight of the first agent, good applicability to the hair is not obtained. In order to obtain better applicability to the hair, the content of the higher alcohol having 20 or more carbon atoms is preferably 0.8% by weight or less, more preferably 0.5% by weight or less, and further preferably 0.1% by weight or less based on the weight of the first agent. Particularly, it is preferable that the two-part hair cosmetic material of the present invention does not contain a higher alcohol having 20 or more carbon atoms since better applicability to the hair and comb through property are obtained.

When the two-part hair cosmetic material of the present invention contains two or more higher alcohols as the ingredient (B), it can contain a combination of alcohols at any ratio.

Examples of the polyoxyethylene alkyl ether having a polyoxyethylene chain length shorter than the polyoxyethylene chain length of the polyoxyethylene alkyl ether (A) as the ingredient (C) include polyoxyethylene isostearyl ether, polyoxyethylene isocetyl ether, polyoxyethylene octyl dodecyl ether, polyoxyethylene oleyl ether, polyoxyethylene oleyl cetyl ether, polyoxyethylene stearyl ether, polyoxyethylene cetyl ether, polyoxyethylene cetostearyl ether, polyoxyethylene tridecyl ether, polyoxyethylene butyl ether, polyoxyethylene behenyl ether, polyoxyethylene myristyl ether, polyoxyethylene lauryl ether, polyoxyethylene octyl phenyl ether, polyoxyethylene dinonyl phenyl ether, and polyoxyethylene nonyl phenyl ether. Particularly, a polyoxyethylene alkyl ether having an HLB of 15 or more is preferable since emulsion stability is better, and the effect of reducing an irritating smell due to ammonia is higher. Examples of the polyoxyethylene alkyl ether having an HLB of 15 or more include polyoxyethylene (40) cetyl ether, polyoxyethylene (20) stearyl ether, and polyoxyethylene (30) cetostearyl ether. The cosmetic material may contain these polyoxyethylene alkyl ethers alone, or may contain a combination of two or more kinds thereof. In addition, when both of the first agent and the second agent contain the polyoxyethylene alkyl ether of the ingredient (C), they may contain the same polyoxyethylene alkyl ether, or may contain different polyoxyethylene alkyl ethers.

The content of the ingredient (C) is not particularly limited. However, the content is preferably 0.1% by weight or more, and more preferably 0.5% by weight or more based on the total weight of the first agent and the second agent since the effect of reducing an irritating smell due to ammonia is higher, and better emulsion stability can be ensured. On the other hand, the content of the ingredient (C) is preferably 10% by weight or less, and more preferably 8% by weight or less based on the total weight of the first agent and the second agent since the effect of reducing an irritating smell due to ammonia is higher, and better emulsion stability can be ensured.

Dye

When the two-part hair cosmetic material of the present invention is a two-part hair cosmetic material for hair dyeing, the first agent contains an oxidation dye and a direct dye which are usually used in the field of two-part hair cosmetic materials.

The oxidation dye is not particularly limited, and examples thereof include 5-aminoorthocresol, 5-aminoorthocresol sulfate, 2,4-diaminophenol hydrochloride, toluene-2,5-diamine hydrochloride, paraphenylenediamine hydrochloride, N-phenylparaphenylenediamine hydrochloride, metaphenylenediamine hydrochloride, orthoaminophenol, N-phenylparaphenylenediamine acetate, 2,6-diaminopyridine, 2,6-diaminopyridine sulfate, 1,5-dihydroxynaphthalene, diphenylamine, toluene-2,5-diamine, toluene-3,4-diamine, α-naphthol, paraaminophenol, paraphenylenediamine, paramethylaminophenol, hydroquinone, pyrogallol, N-phenylparaphenylenediamine, phloroglucin, metaaminophenol, metaphenylenediamine, gallic acid, orthoaminophenol sulfate, orthochloroparaphenylenediamine sulfate, 4,4'-diaminodiphenylamine sulfate, toluene-2,5-diamine sulfate, paraaminophenol sulfate, paraphenylenediamine sulfate, paramethylaminophenol sulfate, 1-hydroxyethyl-4,5-diaminopyrazole sulfate, 2-(2-hydroxyethyl)-1,4-phenylenediammonium sulfate, 2-methylresorcinol, metaaminophenol sulfate, metaphenylenediamine sulfate, and resorcin. The cosmetic material may contain these dyes alone, or may contain a combination of two or more kinds thereof.

The direct dye is not particularly limited, and examples thereof include 2-amino-4-nitrophenol, 2-amino-5-nitrophenol, nitroparaphenylenediamine hydrochloride, nitroparaphenylenediamine, paranitroorthophenylenediamine, 2-amino-5-nitrophenol sulfate, nitroparaphenylenediamine sulfate, paranitroorthophenylenediamine sulfate, paranitroametaphenylenediamine sulfate, 1-amino-4-methylaminoanthraquinone, 1,4-diaminoanthraquinone, picramic acid, sodium picramate, and 2((2-nitrophenyl)amino)ethanol. The cosmetic material may contain these dyes alone, or may contain a combination of two or more kinds thereof.

Since the oxidation dye has higher fastness to hair washing as compared with the direct dye, it is preferable to use only the oxidation dye, or use the oxidation dye and the direct dye in combination as the dye.

The content of the dye is not particularly limited, but is preferably 0.01% by weight or more based on the total weight of the first agent and the second agent. On the other hand, the content of the dye is preferably 15% by weight or less, and more preferably 10% by weight or less based on the total weight of the first agent and the second agent since the hair dyeing power is hardly improved any more even when the dye is contained in an amount exceeding 15% by weight.

The two-part hair cosmetic material of the present invention may contain, in addition to the above-mentioned ingredients, ingredients and additives which are conventionally used in cosmetics. Examples of the ingredients and additives include a surfactant, an oil agent, a polyhydric alcohol, a stabilizer, an antioxidant, a sequestering agent, a solvent, and a buffer. The cosmetic material can appropriately contain these ingredients in any combination as far as the effect of the present invention is not impaired.

Surfactant

In the two-part hair cosmetic material of the present invention, the first agent contains surfactants of the ingredient (A) and the ingredient (C), and may contain a surfactant other than the surfactants of the ingredient (A) and the ingredient (C), in order to obtain sufficient emulsion stability, operability and dyeability. Examples of the different surfactant include a nonionic surfactant, a cationic surfactant, an anionic surfactant, and an amphoteric surfactant. The two-part hair cosmetic material of the present invention may contain one or more of the different surfactants in one or both of the first agent and the second agent of the two-part hair cosmetic material of the present invention. Alternatively, the second agent of the two-part hair cosmetic material of the present invention may contain one or more selected from the surfactants of the ingredient (A) and the ingredient (C) as well as the different surfactants.

It is particularly preferable that the first agent of the two-part hair cosmetic material of the present invention contains a cationic surfactant since better hair touch after hair dyeing or bleaching, and better emulsion stability of the first agent are obtained.

Examples of the cationic surfactant include lanolin fatty acid aminopropylethyldimethylammonium ethyl sulfate, behenyltrimethylammonium chloride, octadecylammonium chloride, octyldihydroxyethylmethylammonium chloride, dialkyl (12-15) dimethylammonium chloride, dialkyl (14-18) dimethylammonium chloride, dicocoyldimethylammonium chloride, distearyldimethylammonium chloride, dicetyldimethylammonium chloride, di(polyoxyethylene) oleylmethylammonium chloride, stearyldihydroxyethylbetaine sodium chloride, stearyldimethylbenzylammonium chloride, stearyltrimethylammonium chloride, cetyltrimethylammonium chloride, cetylpyridinium chloride, benzalkonium chloride, benzethonium chloride, polyoxyethylene (1) polyoxypropylene (25) diethylmethylammonium chloride, myristyldimethylbenzylammonium chloride, methylbenzethonium chloride, lauryltrimethylammonium chloride, laurylpyridinium chloride, alkylisoquinolinium bromide, stearyltrimethylammonium bromide, cetyltrimethylammonium bromide, lauryltrimethylammonium bromide, stearyltrimethylammonium saccharin, and cetyltrimethylammonium saccharin. It is more preferable that the first agent of the two-part hair cosmetic material of the present invention contains an alkyltrimethylammonium salt, and it is particularly preferable that the first agent contains stearyltrimethylammonium chloride, cetyltrimethylammonium chloride, stearyltrimethylammonium bromide or cetyltrimethylammonium bromide, since better hair touch after hair dyeing or bleaching and better emulsion stability of the first agent are obtained.

Further, it is preferable that the two-part hair cosmetic material of the present invention contains a nonionic surfactant since emulsion stability of a preparation is more improved.

The content of a surfactant other than the surfactants of the ingredient (A) and the ingredient (C) contained in the first agent among the surfactants contained in the hair cosmetic material of the present invention (i.e. different surfactants contained in the first agent and/or the second agent and the surfactants of the ingredient (A) and/or the ingredient (C) contained in the second agent) is not particularly limited as far as the effect of the present invention is not impaired. However, the content is preferably 0.1% by weight or more, and more preferably 0.5% by weight or more based on the total weight of the first agent and the second agent since better emulsion stability, operability, dyeability, and better hair touch after hair dyeing or bleaching can be obtained. On the other hand, the content is preferably 10% by weight or less, and more preferably 8% by weight or less since better emulsion stability, operability, dyeability, and better hair touch after hair dyeing or bleaching can be obtained.

Oil Agent

In the two-part hair cosmetic material of the present invention, at least one of the first agent and the second agent may contain an oil agent in order to impart moisturizing, moisture retention, and softening effect to the hair. Examples of the oil agent include fats and oils such as olive oil, sesame oil, castor oil, coconut oil, avocado oil, macadamia nut oil, and shea butter, hydrocarbons such as liquid paraffin, light isoparaffin, solid paraffin, vaseline, microcrystalline wax, and squalane, higher fatty acids such as lauric acid, myristic acid, stearic acid, and oleic acid, and esters such as jojoba oil, isopropyl myristate, isopropyl palmitate, isocetyl isostearate, decyl oleate, and myristyl lactate. Other examples include silicones such as high-polymerization methylpolysiloxane, dimethylsiloxane, a methyl(polyoxyethylene)siloxane copolymer, methylphenylpolysiloxane, and amino-modified silicone.

The two-part hair cosmetic material of the present invention may contain these oil agents alone, or may contain a combination of two or more kinds thereof. The content of the oil agent is not particularly limited as far as the effect of the present invention is not impaired. However, the content is preferably 0.01% by weight or more, and more preferably 0.1% by weight or more based on the total weight of the first agent and the second agent in order to impart a moisturizing, moisture retention, and softening effect to the hair. On the other hand, the content is preferably 10% by weight or less, and more preferably 8% by weight or less based on the total weight of the first agent and the second agent since the more moisturizing, moisture retention, and softening effect is hardly improved any more even when the oil agent is contained in an amount exceeding 10% by weight.

Polyhydric Alcohol

In the two-part hair cosmetic material of the present invention, at least one of the first agent and the second agent may contain a polyhydric alcohol in order to improve low temperature stability, solubility of a dye, applicability to the hair and comb through property. Examples of the polyhydric alcohol include ethylene glycol, propylene glycol, glycerin, polyethylene glycol, ethylene glycol monoethyl ether, ethylene glycol monobutyl ether, and 1,3-butylene glycol.

The two-part hair cosmetic material of the present invention may contain these polyhydric alcohols alone, or may contain a combination of two or more kinds thereof. The content thereof is not particularly limited as far as the effect of the present invention is not impaired. However, the content is preferably 0.1% by weight or more, and more preferably 0.5% by weight or more based on the total weight of the first agent and the second agent in order to obtain better low temperature stability and solubility of a dye. On the other hand, the content is preferably 30% by weight or less, and more preferably 20% by weight or less based on the total weight of the first agent and the second agent since the low temperature stability and solubility of a dye are hardly improved any more even when the polyhydric alcohol is contained in an amount exceeding 30% by weight.

Stabilizer

In the two-part hair cosmetic material of the present invention, the second agent may contain a stabilizer in order to improve stability of hydrogen peroxide. Examples of the stabilizer include phosphoric acid, pyrophosphoric acid, trisodium phosphate, sodium pyrophosphate, acetoanilide, sodium stannate, hydroxyethanediphosphonic acid, and phenoxyethanol.

The two-part hair cosmetic material of the present invention may contain these stabilizers alone, or may contain a combination of two or more kinds thereof. The content of the stabilizer is not particularly limited as far as the effect of the present invention is not impaired, but the content is preferably 0.00005% by weight or more, and more preferably 0.0001% by weight or more based on the total weight of the first agent and the second agent in order to more improve stability of hydrogen peroxide. On the other hand, the content is preferably 5% by weight or less, and more preferably 2% by weight or less based on the total amount of the first agent and the second agent since stability of hydrogen peroxide is hardly improved any more even when the stabilizer is contained in an amount exceeding 5% by weight.

Antioxidant and Sequestering Agent

When the two-part hair cosmetic material of the present invention contains, for example, an oxidation dye, it may contain an antioxidant in order to suppress the oxidation dye from being oxidized to develop a color before the first agent and the second agent are mixed together for use. Examples of the antioxidant include thioglycolic acid, calcium thioglycolate, ammonium thioglycolate, sodium sulfite, ascorbic acid, sodium ascorbate, ammonium ascorbate, propyl gallate, tocopherol, L-cysteine, homocysteine, and N-acetyl-L-cysteine. For example, when the two-part hair cosmetic material contains the oxidation dye, the cosmetic material may contain a sequestering agent in order to prevent color development of the oxidation dye by a metal ion before the first agent and the second agent are mixed together for use. Examples of the sequestering agent include edetic acid, disodium edetate, tetrasodium edetate, sodium metaphosphate, sodium polyphosphate, and sodium citrate.

Solvent and Buffer

The two-part hair cosmetic material of the present invention may contain a solvent and a buffer in order to improve solubility of ingredients such as a dye. Examples of the solvent include alcohols such as ethanol and isopropyl alcohol. Examples of the buffer include ammonium salts such as ammonium bicarbonate and ammonium chloride, and carbonates such as potassium carbonate and sodium carbonate.

Other Ingredients

The two-part hair cosmetic material of the present invention may contain, in addition to the above-mentioned ingredients, ingredients and additives which are conventionally used in cosmetics, such as a hair protective agent, a thickener, a wetting agent, a penetrant, an ultraviolet absorbing agent, an antiseptic agent, a pH adjusting agent, a perfume, a coloring material, and a hair tonic. The two-part hair cosmetic material of the present invention can appropriately contain these ingredients and additives in any combination as far as the effect of the present invention is not impaired.

Viscosity

The viscosity of the first agent or the second agent of the two-part hair cosmetic material of the present invention, or a hair cosmetic material obtained by mixing the first agent and the second agent together is not particularly limited as far as the effect of the present invention is not impaired. The viscosity can be appropriately selected depending on the dosage form as far as dripping or scattering does not occur, in order to attain better mixability, applicability and comb through property.

The hair cosmetic material obtained by mixing the first agent and the second agent together preferably has a viscosity of 1000 mPa·s or more, and more preferably has a viscosity of 3000 mPa·s or more, from the view point of the ease of mixing the first agent and the second agent together, the ease of taking out of a container, applicability to the hair, comb through property after being allowed to stand, and dripping during treatment. On the other hand, the hair cosmetic material preferably has a viscosity of 15000 mPa·s or less, and more preferably has a viscosity of 8000 mPa·s or less. Herein, the viscosity is a value after rotation at 20° C. and 30 rpm for 1 minute using a rotor M4 in a TVB-10-type viscometer (Toki Sangyo Co., Ltd.). Measurement of the viscosity can be performed, for example, by weighing the first agent and the second agent adjusted to 20° C. to have a weight ratio of 1:2, mixing the agents sufficiently to be uniform to obtain a hair cosmetic material, and putting the hair cosmetic material into an appropriate container for measurement. The mixing method can be appropriately selected depending on the dosage form thereof, and the first agent and the second agent may be placed into an appropriate container and mixed together using a brush, or a method of placing the agents into a bottle and shaking the bottle may be employed.

Preparation Method

The two-part hair cosmetic material of the present invention can be prepared by a publicly known method. For example, by dissolving and mixing the ingredients in water, or if necessary, warming a part of ingredients, stirring them to mix, thereafter, cooling the mixture, adding the remaining ingredients thereto, and stirring them to mix, a first agent and a second agent can be prepared. As water, purified water is usually used. The content of water is the remnant of predetermined amounts of respective ingredients contained, and is preferably around 10% by weight or more and around 95% by weight or less based on the total weight of the first agent or the second agent, respectively. The content is appropriately adjusted according to the kind, content and the like of respective ingredients.

Method of Use

The two-part hair cosmetic material in the present invention can be used in bleaching or dyeing by a publicly known method, for example, a method of mixing the first agent and the second agent together immediately before use, and applying the mixture to the hair. The bleaching or dyeing time is appropriately adjusted according to the contents of ammonia and an oxidizing agent, kind and an amount of an oxidation dye, application amount to the hair, and desired degree of dyeing, and is usually 5 minutes or longer, preferably 5 to 50 minutes, and more preferably 10 to 45 minutes.

The two-part hair cosmetic material of the present invention can be formulated into a dosage form such as a cream, a liquid, a gel, or a foam as far as the effect of the present invention is not impaired, but the dosage form is not limited to these. Further, the first agent and the second agent may be in different dosage forms, for example, the first agent being a cream and the second agent being a liquid, and the mixing ratio between the first agent and the second agent is not limited.

The two-part hair cosmetic material of the present invention can be used by mixing the first agent and the second agent together by a conventional method in accordance with the dosage form as far as the effect of the present invention is not impaired. For example, a variety of methods such as a method of mixing the first agent and the second agent together to be uniform using a brush, a muddler, a spatula or the like in a container such as a tray, and applying the mixture to the hair using an application tool such as a brush or a comb, or by hand, and a method of placing the first agent and the second agent into a bottle having a sufficient volume, shaking the bottle to mix them to be uniform, and applying the mixture to the hair using an applicator for application (single nozzle, comb-type nozzle etc.), an application tool such as a brush or a comb, or by hand can be appropriately selected.

EXAMPLES

Then, examples of the present invention as well as comparative examples will be described, but the present invention is not limited to the following examples. In the following examples and comparative examples, the content is shown by % by weight.

First agents of hair dyes having the compositions shown in Examples 1 to 10 and Comparative Examples 1 to 5 of Table 1 and Table 2, and a first agent of a bleaching agent having the composition shown in Example 11 of Table 2 were prepared by a conventional method. In addition, a second agent having the composition shown in Table 3 was prepared by a conventional method. Regarding the first agents, emulsion stability was evaluated by the evaluation method shown below.

Method of Evaluating Emulsion Stability

After the prepared composition of the first agent was allowed to stand at room temperature for 1 month, the emulsified state of the composition was observed visually. The obtained results are shown in Table 1 and Table 2.

In Table 1 and Table 2, each mark shows the following result.

⊙: The emulsified state is extremely good, and no change is recognized.

○: The emulsified state is good, and no change is recognized.

Δ: The emulsified state is rough, and separation of water or an oil is slightly recognized.

×: The emulsified state is poor, and separation of water or an oil is recognized.

Each of the first agents was mixed with the second agent having the composition shown in Table 3 to prepare a hair cosmetic material, and an irritating smell due to ammonia, applicability of the hair cosmetic material obtained by mixing the agents together to the hair, and comb through property after the hair cosmetic material is allowed to stand were evaluated by the following methods.

Method of Evaluating Irritating Smell Due to Ammonia

The prepared first agent and second agent were sufficiently mixed together using a brush at a weight ratio of 1:2 at room temperature immediately before use until unevenness disappeared, and thereby, a sample was obtained. While each sample was further mixed using a brush a few times for evaluation, an irritating smell due to ammonia was evaluated sensory.

The obtained results are shown in Table 1 and Table 2.

In Table 1 and Table 2, each mark shows the following result.

⊙: The irritating smell is weak.

○: The irritating smell is slightly weak.

Δ: The irritating smell is slightly strong.

×: The irritating smell is strong.

Method of Evaluating Applicability of Hair Cosmetic Material to Hair

Into a plastic bottle having a volume of 200 mL, each 40 g and 80 g of the prepared first agent and second agent were placed, the bottle was closed with a lid, and the container was shaken up and down about 30 times to mix the first agent and the second agent together. The lid of the plastic bottle containing the mixed liquid was replaced with a comb-type nozzle, and the mixed liquid discharged from the nozzle was applied to a hair wig having a length of about 30 cm. Ease of application when the mixed liquid was applied to the hair wig was evaluated sensory.

The obtained results are shown in Table 1 and Table 2.

In Table 1 and Table 2, each mark shows the following result.
⊙: Application is easy.
○: Application is slightly easy.
△: Application is slightly difficult.
×: Application is difficult.

Method of Evaluating Comb Through Property after Hair Cosmetic Material was Allowed to Stand Into a plastic bottle having a volume of 200 mL, each 40 g and 80 g of the prepared first agent and second agent were placed, the bottle was closed with a lid, and the container was shaken up and down about 30 times to mix the first agent and the second agent together. The lid of the plastic bottle containing the mixed liquid was replaced with a comb-type nozzle, and the mixed liquid discharged from the nozzle was applied to a hair wig having a length of about 30 cm and allowed to stand for 20 minutes. After being allowed to stand, the wig was combed with a large-tooth comb, and combability (comb through property) was evaluated sensory.

The obtained results are shown in Table 1 and Table 2.

In Table 1 and Table 2, each mark shows the following result.
⊙: Combing is easy.
○: Combing is slightly easy.
△: Combing is slightly difficult.
×: Combing is difficult.

TABLE 1

| | [First agent] | | | | | | | |
|---|---|---|---|---|---|---|---|---|
| | Example | | | | | | | |
| Raw material | 1 | 2 | 3 | 4 | 5 | 6 | 7 | 8 |
| POE (100) stearyl ether | 1.50 | — | — | 1.50 | 1.50 | 1.50 | 1.50 | 1.50 |
| POE (55) cetostearyl ether | — | 1.50 | — | — | — | — | — | — |
| POE (80) stearyl ether | — | — | 1.50 | — | — | — | — | — |
| POE (30) cetostearyl ether | 1.50 | 1.50 | 1.50 | 1.50 | 1.50 | 1.50 | 1.50 | 1.50 |
| Myristyl alcohol | — | — | — | 3.00 | 3.00 | 6.00 | — | — |
| Cetanol | 3.00 | 3.00 | 3.00 | 3.00 | — | — | 6.00 | — |
| Stearyl alcohol | 3.00 | 3.00 | 3.00 | — | 3.00 | — | — | 6.00 |
| Behenyl alcohol | — | — | — | — | — | — | — | — |
| Stearyltrimethylammonium chloride | 0.960 | 0.960 | 0.960 | 0.960 | 0.960 | 0.960 | 0.960 | 0.960 |
| Liquid paraffin | 3.00 | 3.00 | 3.00 | 3.00 | 3.00 | 3.00 | 3.00 | 3.00 |
| Glycerin | 2.00 | 2.00 | 2.00 | 2.00 | 2.00 | 2.00 | 2.00 | 2.00 |
| Tetrasodium edetate | 0.20 | 0.20 | 0.20 | 0.20 | 0.20 | 0.20 | 0.20 | 0.20 |
| Anhydrous sodium sulfite | 0.40 | 0.40 | 0.40 | 0.40 | 0.40 | 0.40 | 0.40 | 0.40 |
| Ascorbic acid | 0.30 | 0.30 | 0.30 | 0.30 | 0.30 | 0.30 | 0.30 | 0.30 |
| Dimethyldiallylammonium chloride-acrylic acid copolymer liquid | 1.00 | 1.00 | 1.00 | 1.00 | 1.00 | 1.00 | 1.00 | 1.00 |
| Paraaminophenol | 0.18 | 0.18 | 0.18 | 0.18 | 0.18 | 0.18 | 0.18 | 0.18 |
| 5-Aminoorthocresol | 0.23 | 0.23 | 0.23 | 0.23 | 0.23 | 0.23 | 0.23 | 0.23 |
| Toluene-2,5-diamine sulfate | 0.05 | 0.05 | 0.05 | 0.05 | 0.05 | 0.05 | 0.05 | 0.05 |
| Amino-modified silicone | 1.00 | 1.00 | 1.00 | 1.00 | 1.00 | 1.00 | 1.00 | 1.00 |
| Strong aqueous ammonia (28%) | 7.50 | 7.50 | 7.50 | 7.50 | 7.50 | 7.50 | 7.50 | 7.50 |
| Purified water | Balance | Balance | Balance | Balance | Balance | Balance | Balance | Balance |
| Mixing ratio (first agent:second agent) | | | | 1:2 | | | | |
| Emulsion stability of first agent | ⊙ | ○ | ○ | ⊙ | ⊙ | ○ | ○ | ⊙ |
| Irritating smell due to ammonia | ⊙ | ⊙ | ⊙ | ○ | ⊙ | ○ | ○ | ⊙ |
| Applicability to hair | ⊙ | ⊙ | ⊙ | ⊙ | ○ | ○ | ⊙ | ○ |
| Comb through property after being allowed to stand | ⊙ | ○ | ○ | ⊙ | ⊙ | ○ | ○ | ○ |

TABLE 1-continued

[First agent]

| | Example | | | | | | | |
|---|---|---|---|---|---|---|---|---|
| Raw material | 1 | 2 | 3 | 4 | 5 | 6 | 7 | 8 |
| Viscosity of hair cosmetic material obtained by mixing first agent and second agent together (mPa · s) | 5920 | — | — | 4390 | 3970 | — | — | — |

TABLE 2

[First agent]

| | Example | | | Comparative Example | | | | |
|---|---|---|---|---|---|---|---|---|
| Raw material | 9 | 10 | 11 | 1 | 2 | 3 | 4 | 5 |
| POE (100) stearyl ether | 1.50 | 1.50 | 1.50 | — | 3.00 | 1.50 | 1.50 | 1.50 |
| Lipophilic glyceryl monostearate | — | — | — | — | — | 1.50 | — | — |
| POE (30) cetostearyl ether | 1.50 | 1.50 | 1.50 | 3.00 | — | — | 1.50 | 1.50 |
| Myristyl alcohol | — | — | — | — | — | — | — | — |
| Cetanol | 3.00 | 2.60 | 3.00 | 3.00 | 3.00 | 3.00 | 2.40 | 2.00 |
| Stearyl alcohol | 3.00 | 2.60 | 3.00 | 3.00 | 3.00 | 3.00 | 2.40 | 2.00 |
| Behenyl alcohol | — | 0.80 | — | — | — | — | 1.20 | 2.00 |
| Stearyltrimethylammonium chloride | 0.960 | 0.960 | 0.960 | 0.960 | 0.960 | 0.960 | 0.960 | 0.960 |
| Liquid paraffin | — | 3.00 | 3.00 | 3.00 | 3.00 | 3.00 | 3.00 | 3.00 |
| Isopropyl palmitate | 3.00 | — | — | — | — | — | — | — |
| Glycerin | 2.00 | 2.00 | 2.00 | 2.00 | 2.00 | 2.00 | 2.00 | 2.00 |
| Tetrasodium edetate | 0.20 | 0.20 | 0.20 | 0.20 | 0.20 | 0.20 | 0.20 | 0.20 |
| Anhydrous sodium sulfite | 0.40 | 0.40 | 0.40 | 0.40 | 0.40 | 0.40 | 0.40 | 0.40 |
| Ascorbic acid | 0.30 | 0.30 | 0.30 | 0.30 | 0.30 | 0.30 | 0.30 | 0.30 |
| Dimethyldiallylammonium chloride-acrylic acid copolymer liquid | 1.00 | 1.00 | 1.00 | 1.00 | 1.00 | 1.00 | 1.00 | 1.00 |
| Paraaminophenol | 0.18 | 0.18 | — | 0.18 | 0.18 | 0.18 | 0.18 | 0.18 |
| 5-Aminoorthocresol | 0.23 | 0.23 | — | 0.23 | 0.23 | 0.23 | 0.23 | 0.23 |
| Toluene-2,5-diamine sulfate | 0.05 | 0.05 | — | 0.05 | 0.05 | 0.05 | 0.05 | 0.05 |
| Amino-modified silicone | 1.00 | 1.00 | 1.00 | 1.00 | 1.00 | 1.00 | 1.00 | 1.00 |
| Strong aqueous ammonia (28%) | 7.50 | 7.50 | 7.50 | 7.50 | 7.50 | 7.50 | 7.50 | 7.50 |
| Purified water | Balance | Balance | Balance | Balance | Balance | Balance | Balance | Balance |
| Mixing ratio (first agent:second agent) | | | | 1:2 | | | | |
| Emulsion stability of first agent | ⊙ | ○ | ⊙ | Δ | X | X | ○ | ○ |
| Irritating smell due to ammonia | ⊙ | ○ | ⊙ | ○ | X | X | ○ | ○ |
| Applicability of hair cosmetic material to hair | ○ | ○ | ○ | Δ | Δ | X | Δ | Δ |
| Comb through property after being allowed to stand | ○ | ○ | ○ | Δ | ○ | X | Δ | X |
| Viscosity of hair cosmetic material obtained by mixing first agent and second agent together (mPa · s) | 7840 | 5860 | 5680 | 5970 | 3820 | — | 5760 | — |

TABLE 3

[Second agent]

| Raw material | 1 |
|---|---|
| Lipophilic glyceryl monostearate | 0.50 |
| POE (30) cetostearyl ether | 0.50 |
| Coconut oil fatty acid amidopropylbetaine liquid (30%) | 0.40 |
| Cetanol | 2.00 |
| Stearyl alcohol | 2.00 |
| Liquid paraffin | 0.60 |
| Propylene glycol | 0.50 |
| Hydroxyethanediphosphonic acid liquid (60%) | 0.06 |
| Diethylenetriamine pentaacetic acid pentasodium liquid (40%) | 0.05 |
| Purified water | Balance |
| Aqueous hydrogen peroxide (35%) | 16.60 |

From the above-mentioned results, it is seen that the two-part hair cosmetic material of the present invention has good emulsion stability, is reduced in the irritating smell due to ammonia, and is good in applicability of a hair cosmetic material obtained by mixing the first agent and the second agent together to the hair, and comb through property.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A two-part hair cosmetic material comprising a first agent containing an alkali agent and a second agent containing an oxidizing agent, wherein
   the first agent contains the following ingredients:
   (A) a polyoxyethylene alkyl ether having a polyoxyethylene chain length of 55 to 150,
   (B) a higher alcohol, and
   (C) a polyoxyethylene alkyl ether having a polyoxyethylene chain length shorter than the polyoxyethylene chain length of the polyoxyethylene alkyl ether (A), and
   the content of a higher alcohol having 20 or more carbon atoms in the higher alcohol (B) is 1.0% by weight or less based on the weight of the first agent.

2. The two-part hair cosmetic material according to claim 1, wherein the higher alcohol (B) comprises at least two higher alcohols selected from higher alcohols having less than 20 carbon atoms.

3. The two-part hair cosmetic material according to claim 1, wherein the higher alcohol (B) does not comprise a higher alcohol having 20 or more carbon atoms.

4. The two-part hair cosmetic material according to claim 1, wherein the first agent further comprises a cationic surfactant.

5. The two-part hair cosmetic material according to claim 1, wherein the two-part hair cosmetic material is a two-part hair cosmetic material for dyeing.

6. The two-part hair cosmetic material according to claim 1, wherein the polyoxyethylene alkyl ether (A) has a polyoxyethylene chain length of 80 to 150.

7. The two-part hair cosmetic material according to claim 1, wherein the polyoxyethylene alkyl ether (A) having a polyoxyethylene chain length of 50 or more is selected from the group consisting of: polyoxyethylene (150) cetyl ether, polyoxyethylene (80) stearyl ether, polyoxyethylene (100) stearyl ether, polyoxyethylene (55) cetyl stearyl ether, polyoxyethylene (60) cetyl stearyl ether, polyoxyethylene (80) cetyl stearyl ether, polyoxyethylene (82) oleyl ether, and polyoxyethylene (106) oleyl ether.

8. The two-part hair cosmetic material according to claim 1, wherein the content of the polyoxyethylene alkyl ether (A) having a polyoxyethylene chain length of 50 or more is 0.1% by weight to 10% by weight based on the total weight of the first agent and the second agent.

9. The two-part hair cosmetic material according to claim 1, wherein the content of the polyoxyethylene alkyl ether (A) having a polyoxyethylene chain length of 50 or more is 0.5% by weight to 8% by weight, based on the total weight of the first agent and the second agent.

10. The two-part hair cosmetic material according to claim 1, wherein the higher alcohol (B) is selected from lauryl alcohol, myristyl alcohol, cetanol, stearyl alcohol, cetostearyl alcohol, behenyl alcohol, isostearyl alcohol, oleyl alcohol, hexyldecanol, and octyldodecanol.

11. The two-part hair cosmetic material according to claim 1, wherein the content of the higher alcohol (B) is 1.0% by weight to 20% by weight, based on the total weight of the first agent and the second agent.

12. The two-part hair cosmetic material according to claim 1, wherein the polyoxyethylene alkyl ether (C) having a polyoxyethylene chain length shorter than the polyoxyethylene chain length of the polyoxyethylene alkyl ether (A) is selected from the group consisting of: polyoxyethylene (40) cetyl ether, polyoxyethylene (20) stearyl ether, and polyoxyethylene (30) cetostearyl ether.

13. The two-part hair cosmetic material according to claim 1, wherein the content of the polyoxyethylene alkyl ether (C) having a polyoxyethylene chain length shorter than the polyoxyethylene chain length of the polyoxyethylene alkyl ether (A) is 0.1% by weight to 10% by weight, based on the total weight of the first agent and the second agent.

14. The two-part hair cosmetic material according to claim 1, wherein the content of the polyoxyethylene alkyl ether (C) having a polyoxyethylene chain length shorter than the polyoxyethylene chain length of the polyoxyethylene alkyl ether (A) is 0.5% by weight to 8% by weight, based on the total weight of the first agent and the second agent.

15. The two-part hair cosmetic material according to claim 1, wherein it contains 0.1% by weight to 10% by weight, in terms of 28% aqueous ammonia, based on the total weight of the first agent and the second agent.

16. The two-part hair cosmetic material according to claim 1, wherein it contains 1% by weight to 7% by weight, in terms of 28% aqueous ammonia, based on the total weight of the first agent and the second agent.

17. The two-part hair cosmetic material according to claim 1, wherein it contains 2% by weight to 7% by weight, in terms of 28% aqueous ammonia, based on the total weight of the first agent and the second agent.

18. The two-part hair cosmetic material according to claim 1, wherein the content of water is 10% by weight to 95% by weight, based on the total weight of the first agent or the second agent.

19. The two-part hair cosmetic material according to claim 1, further comprising 0.01% by weight to 10% by weight of an oil agent, based on the total weight of the first agent and the second agent.

* * * * *